(12) United States Patent
Haaring

(10) Patent No.: US 10,736,287 B2
(45) Date of Patent: Aug. 11, 2020

(54) DARK STEM CUCUMBER PLANTS

(71) Applicant: RIJK ZWAAN ZAADTEELT EN ZAADHANDEL B.V., De Lier (NL)

(72) Inventor: Cornelis Haaring, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 14/841,880

(22) Filed: Sep. 1, 2015

(65) Prior Publication Data

US 2016/0014989 A1 Jan. 21, 2016

Related U.S. Application Data

(63) Continuation-in-part of application No. PCT/EP2014/054722, filed on Mar. 11, 2014, which is a continuation of application No. 13/793,008, filed on Mar. 11, 2013, now abandoned.

(30) Foreign Application Priority Data

Mar. 11, 2013 (EP) .................................... 13158611

(51) Int. Cl.
*A01H 5/08* (2018.01)
*A01H 4/00* (2006.01)
*A01H 5/00* (2018.01)
*A23L 19/00* (2016.01)

(52) U.S. Cl.
CPC ............... *A01H 5/08* (2013.01); *A01H 4/005* (2013.01); *A01H 5/00* (2013.01); *A23L 19/00* (2016.08); *A23V 2002/00* (2013.01)

(58) Field of Classification Search
None
See application file for complete search history.

(56) References Cited

U.S. PATENT DOCUMENTS

| | | | |
|---|---|---|---|
| 8,247,645 B2 | 8/2012 | Mullor Torres et al. | |
| 8,872,003 B2 | 10/2014 | Kloet et al. | |
| 2010/0170001 A1 | 7/2010 | Mullor Torres et al. | |
| 2011/0277191 A1 | 11/2011 | Kloet et al. | |
| 2012/0317669 A1* | 12/2012 | Shetty | A01H 5/08 800/260 |
| 2013/0074223 A1 | 3/2013 | Dirks et al. | |

FOREIGN PATENT DOCUMENTS

| | | |
|---|---|---|
| WO | 2007/042070 | 4/2007 |
| WO | 2010/057960 | 5/2010 |
| WO | 2011/144672 | 11/2011 |

OTHER PUBLICATIONS

International Search Report and Written Opinion of the International Searching Authority dated May 14, 2014, which issued during prosecution of International Application No. PCT/EP2014/054722.
Hovi-Pekkanen, et al. "Effects of interlighting on yield and external fruit quality in year-round cultivated cucumber" Scientia Horticulturae 116(2):152-161, Dec. 2007.
Jolliffe, et al. "Predictors of Shelf Life in Long English Cucumber" Journal of the American Society for Horticultural Science 122(5):686-690, Jan. 1997.
Schouten, et al. "Predicting keeping quality of batches of cucumber fruit based on a physiological mechanism" Postharvest Biology and Technology 26(2):209-220, Sep. 2002.
Rui-Huan, et al. "A New Cucumber F1 Hybrid—'Jinyou No. 49'" China Vegetables, 2012, 10:83-85.

* cited by examiner

*Primary Examiner* — Brent T Page
(74) *Attorney, Agent, or Firm* — Duane Morris LLP; Thomas J. Kowalski; Deborah L. Lu

(57) ABSTRACT

The present invention relates to a cucumber plant of the species *Cucumis sativus* carrying a genetic determinant that leads to a darker green stem in the seedling stage that is predictive of a darker green color of the fruits as compared to an isogenic cucumber plant not carrying the said genetic determinant, which genetic determinant is as comprised in a cucumber plant representative seed of which was deposited with the NCIMB under deposit number NCIMB 41859. The genetic determinant is suitably introgressed into the cucumber plant from a cucumber plant of which representative seed has been deposited with the NCIMB under deposit number NCIMB 41859.

14 Claims, 5 Drawing Sheets

DARK STEM CUCUMBER PLANTS

RELATED APPLICATIONS AND INCORPORATION BY REFERENCE

This application is a continuation-in-part application of international patent application Serial No. PCT/EP2014/054722 filed 11 Mar. 2014, which published as PCT Publication No. WO 2014/140026 on 18 Sep. 2014, which claims benefit of and priority to European patent application Serial No. 13158611.7 filed 11 Mar. 2013 and U.S. patent application Ser. No. 13/793,008 filed 11 Mar. 2013, now abandoned.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a new cucumber plant that produces fruits that have a darker green color as a component of extended storability. The invention also relates to phenotypic and/or molecular markers to predict the darker green color in an early plant stage.

BACKGROUND OF THE INVENTION

The increase of storability of cucumber is traditionally one of the major goals of cucumber breeding. Storability, or shelf life, consists of multiple aspects, the most important one being fruit color. Fruit color as an aspect of extended storability can again be subdivided into two components: the initial fruit color, and the ability to stay green for an extended period of time. Both components are largely influenced by the genetic background of the cucumber plant, but environmental effects also play a role.

During a breeding process, initial fruit color can only be observed phenotypically, in the adult plant stage, after fruit harvest. The development of cucumbers with an improved storability based on an improved initial fruit color is therefore time-consuming, since the breeding cycles are long and many generations are needed to ensure the transfer of the trait. Progress in development for longer shelf-life, i.e. in an increase of days that a cucumber fruit can be stored while the color remains acceptable for consumption, is slow.

Citation or identification of any document in this application is not an admission that such document is available as prior art to the present invention.

SUMMARY OF THE INVENTION

An improved fruit color during storage of cucumber fruits is desirable from a commercial point of view. Various measures are taken post-harvest to reduce deterioration of cucumber fruits, such as shrink-wrapping or wax-coating. From an environmentally conscious perspective shrink-wrapping is undesirable since it leads to additional waste. Both shrink-wrapping and wax-coating also require additional handling of the fruits which incurs costs and can lead to blemishes. The additional material that is needed for these measures adds up to the costs as well.

During research that led to the present invention a new cucumber plant was created, the fruits of which have a darker initial fruit color, which darker fruit color can be predicted phenotypically, and/or genetically through molecular markers, in an early plant stage. The darker fruit color can serve as a component of extended storability It is an object of the present invention to provide cucumber plants that generate fruits with an extended storability.

It is an object of the present invention to provide cucumber plants (*Cucumis sativus*) that carry a genetic determinant which leads to fruits with a darker green color.

It is a further object of the present invention to provide a phenotypic marker to identify cucumber plants in seedling stage that carry the genetic determinant of the invention.

It is an object of the present invention to provide molecular markers to identify the genetic determinant of the invention.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of *Cucumis sativus* EX5004 that comprise the genetic determinant and phenotypic trait of the invention were deposited with NCIMB Ltd, Ferguson Building, Craibstone Estate, Bucksburn, Aberdeen AB21 9YA, UK on 31 Aug. 2011 under deposit accession number NCIMB 41859.

The deposited seeds do not meet the DUS criteria which are required for obtaining plant variety protection, and can therefore not be considered to be plant varieties.

The Deposits with NCIMB Ltd, Ferguson Building, Craibstone Estate, Bucksburn, Aberdeen AB21 9YA, UK, under deposit accession number 41859 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
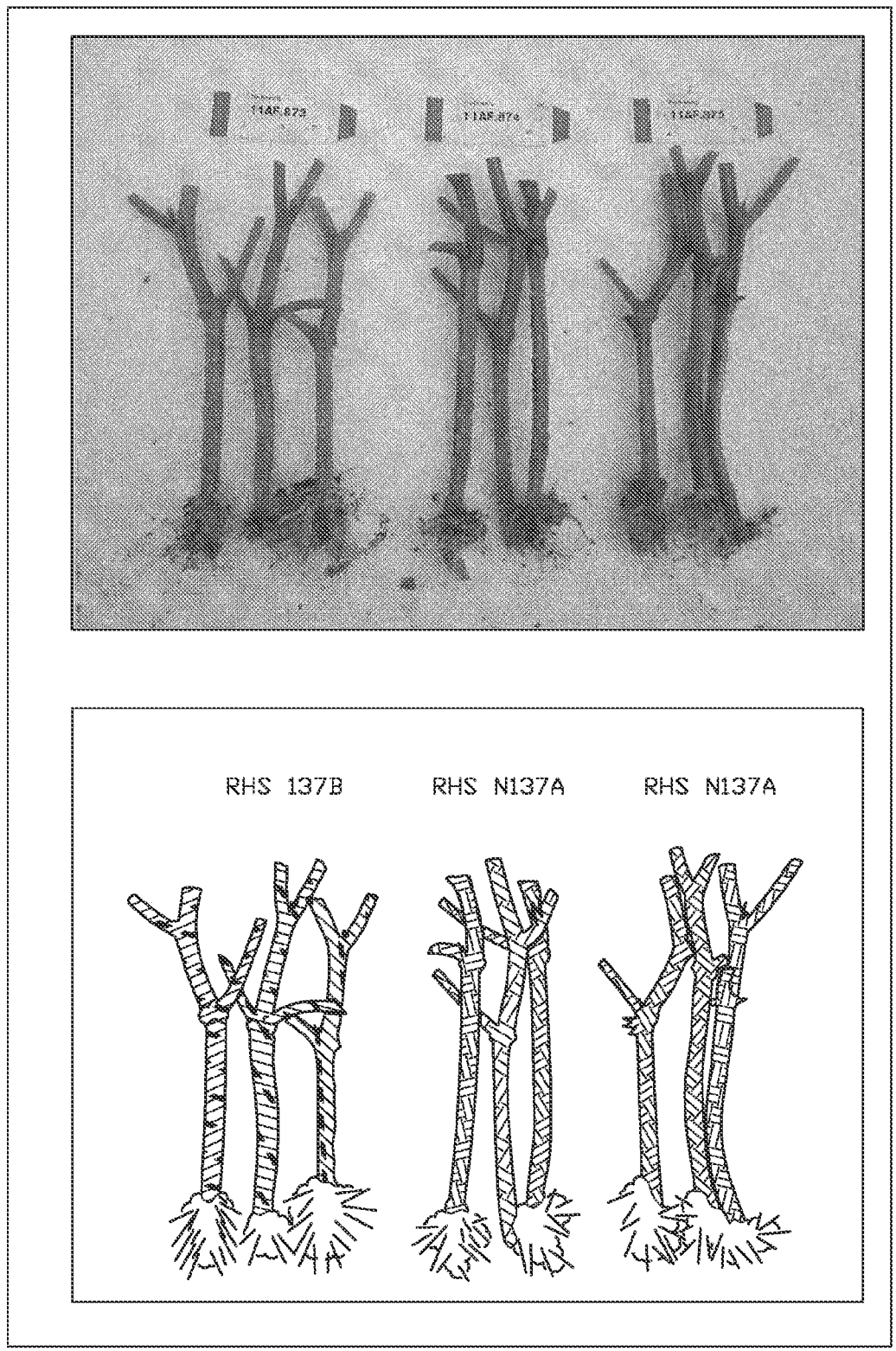
FIG. 1: comparison picture of cucumber dark stem and normal stem. Plant 11AF.873 has a normal stem; plant 11AF.874 has a dark stem and plant 11AF.875 is an F1 from the cross (dark stem×normal stem).

The present invention thus provides a cucumber plant of the species *Cucumis sativus* carrying a genetic determinant that leads to a darker green stem in the seedling stage that is predictive of a darker green color of the fruits as compared to an isogenic cucumber plant not carrying the said genetic determinant, which genetic determinant is as comprised in a cucumber plant representative seed of which was deposited with the NCIMB under deposit number NCIMB 41859.

In one embodiment the genetic determinant that leads to a darker green stem in the seedling stage that is predictive of a darker green color of the fruits as compared to an isogenic cucumber plant not carrying the said genetic determinant is introgressed from a cucumber plant which may comprise said genetic determinant, representative seed of which was deposited with the NCIMB under deposit number NCIMB 41859.

During research that led to the present invention new *Cucumis sativus* plants were created. The seedling stem of the new cucumber plant is chlorophyll rich, which can already be observed within one week after germination. Observation can be done visually, as the stem is very dark green, or the chlorophyll content in the stem can be measured. In a later plant stage both the leaf- and fruit stems also show a darker green color and/or an increase in the chlorophyll content. In the fruit picking stage the fruit color is marked as extremely dark green. In addition, after harvest the fruit has an increased conservation or storability quality. All above mentioned parts of a plant of the invention are darker and/or higher in chlorophyll content as compared to an isogenic cucumber plant grown under the same conditions, which is genetically the same but does not carry the genetic determinant of the invention.

The trait of the present invention is determined by a monogenic dominant or at least incomplete dominant genetic determinant. Therefore the genetic determinant can be present in homozygous or heterozygous state to result in the phenotypic trait of the invention. The fruits carrying the genetic determinant of the invention show a darker green color as compared to cucumber fruits of an isogenic plant not carrying the said genetic determinant.

In one embodiment, the said genetic determinant is linked with any of the polymorphic molecular AFLP markers E13/M51-143.48 and/or E13/M51-154.68 and/or E16/M60-086.74 in a cucumber plant representative seed of which was deposited with the NCIMB under deposit number NCIMB 41859.

The invention also relates to a cucumber plant which may comprise the genetic determinant of the invention, wherein the genetic determinant is linked with any of the molecular markers E13/M51-143.48 and/or E13/M51-154.68 and/or E16/M60-086.74.

The cucumber plant of the invention is obtainable by crossing a first cucumber plant with a second cucumber plant, wherein at least one of the said plants is grown from seed of which a representative sample was deposited with the NCIMB under deposit number NCIMB 41859, or a progeny plant thereof, optionally selfing the resulting F1, and selecting for plants that have one or more of the following characteristics:
a) they have at the seedling stage a darker green stem as compared to the stem of a seedling of an isogenic cucumber plant not carrying the said genetic determinant, which darker green stem is predictive of the production of fruits having a darker green color at harvest stage as compared to the fruits of an isogenic cucumber plant not carrying the said genetic determinant under the same conditions, and/or
b) they have at the seedling stage an increase in the content of chlorophyll in the stem as compared to chlorophyll content in the stem of a seedling of an isogenic cucumber plant not carrying the said genetic determinant, which increase in the content of chlorophyll is predictive of the production of fruits having a darker green color at harvest stage as compared to the fruits of an isogenic cucumber plant not carrying the said genetic determinant under the same conditions.

Either one or both of the first and second cucumber plants used to obtain a cucumber plant of the invention thus carries the said genetic determinant that results in a darker green stem in the seedling stage that is predictive of a darker green color of the fruits.

In the deposited seeds, the genetic determinant is linked with any of the molecular markers E13/M51-143.48 and/or E13/M51-154.68 and/or E16/M60-086.74. This marker can also be linked to the genetic determinant that may be comprised in either or both cucumber plants that are used as parents in a cross to transfer the dark stem phenotype to other plants, but the presence of at least one of the mentioned markers is not essential as long as the genetic determinant causing the phenotype is present. Furthermore, a plant of the invention showing the dark stem phenotype as described herein is still a plant of the invention when the genetic determinant underlying the phenotype is present therein but the markers no longer are.

It is clear that the parent that provides the genetic determinant that leads to the trait of the invention is not necessarily a plant grown directly from the deposited seeds. The parent can also be a progeny plant from the deposited seed, obtained by for example selfing or crossing, or a progeny plant from seeds that are identified to have obtained the genetic determinant that leads to the trait of the invention by other means.

According to a further aspect thereof the invention provides the genetic determinant as defined herein, which genetic determinant is selected from a group which may comprise: a gene, an allele, a gene construct, a QTL, a promoter, an isolated gene, a transgene, a DNA sequence.

Plants of the invention can be identified on the basis of the following selection characteristics:

a) they produce fruits having a darker green color at harvest stage and during storage up to 14 days, preferably up to 17 days, more preferably up to 19 days, most preferably up to 21 days after harvest, as compared to the fruits of an isogenic cucumber plant not carrying the said genetic determinant that is grown and stored under the same conditions, and/or b) they have at the seedling stage a darker green stem as compared to the stem of a seedling of an isogenic cucumber plant not carrying the said genetic determinant, and/or c) they have at the seedling stage an increase in the content of chlorophyll in the stem as compared to the stem of a seedling of an isogenic cucumber plant not carrying the said genetic determinant.

In a preferred embodiment, the occurrence of one or more characteristics in a selected plant is genetically linked with any of the molecular markers E13/M51-143.48 and/or E13/M51-154.68 and/or E16/M60-086.74.

In a cucumber plant of the invention the chlorophyll content in the stem of the plant at seedling stage is at least, in order of increased preference, 40 µg/g, 70 µg/g, 100 µg/g, 120 µg/g, 150 µg/g, 180 µg/g, 200 µg/g higher than the chlorophyll content in the stem of an isogenic cucumber plant at seedling stage not carrying the said genetic determinant, that is grown under the same conditions.

The chlorophyll content in the stem of a cucumber seedling carrying the genetic determinant of the invention is preferably higher than 140 µg/g. The chlorophyll content in the seedling stem is suitably not higher than 1000 µg/g.

In a cucumber plant of the invention the chlorophyll content in the stem of the plant at seedling stage is at least, in order of increased preference, 30% higher, 60% higher, 90% higher, 120% higher, 150% higher, 180% higher, 200% higher, 230% higher, 270% higher, 300% higher than the chlorophyll content in the stem of an isogenic cucumber plant at seedling stage not carrying the said genetic determinant, that is grown under the same conditions.

The darker green stem of a seedling of a cucumber plant of the invention can also be scored visually. On a scale of 1-5, the seedling stem of a cucumber plant of the invention is at least 1 grade darker, preferably at least 2 grades darker, than the color of the stem of an isogenic cucumber plant at seedling stage not carrying the genetic determinant of the invention. To compare the colors of the stem, or to compare the chlorophyll contents, it is essential that the seedlings are grown under the same conditions.

A visual comparison of the stem color at 21 days after sowing is shown schematically in FIG. 1. The actual colors of the seedling stems depicted in FIG. 1 were determined to be 137B for the normal stem and N137A for the dark stem based on the color chart of the Royal Horticultural Society. However, it is not necessary that a plant of the invention has exactly color N137A. A plant of the invention has to have a color that differs from the color of an isogenic plant without the genetic determinant to the same or a similar extent as the difference between 137B and N137A. The RGB, CIELab and CIELCh values for the two colors are listed in the Table 1 below.

TABLE 1

Comparison of color values

| RHS code | sRGB | | | CIE Lab D65/10° | | | CIE LCh D65/10° | | |
|---|---|---|---|---|---|---|---|---|---|
| | R | G | B | L | a | b | L | C | h |
| 137B | 91 | 111 | 81 | 45 | −13 | 14 | 45 | 19 | 134 |
| N137A | 81 | 91 | 69 | 37 | −8 | 11 | 37 | 14 | 127 |

Figure 2A:
FIGS. 2A-2B: chlorophyll measurements of cucumber seedling stems
Figure 2B:
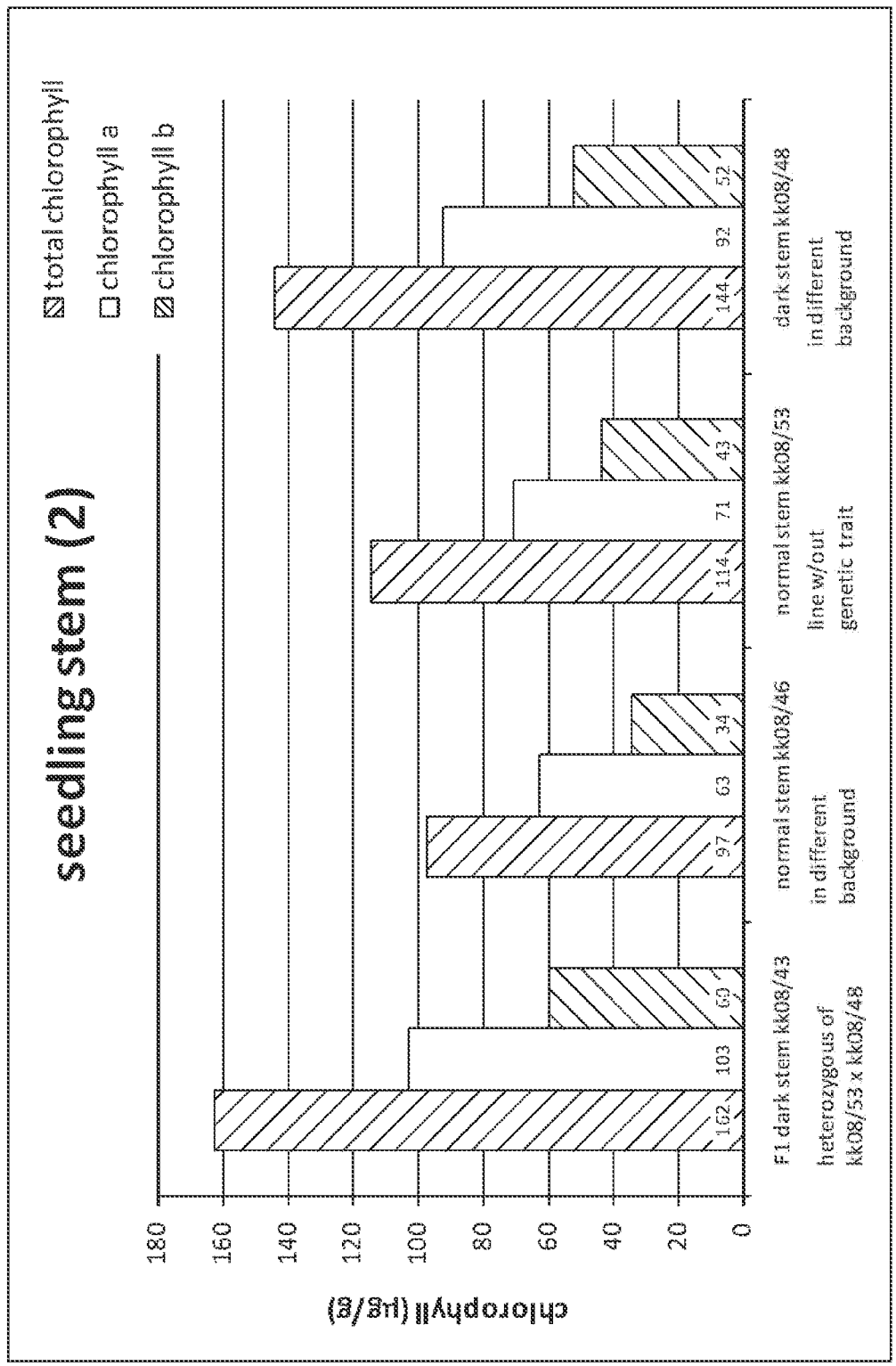

Measurements and comparison of chlorophyll content between seedlings of plants of the invention and isogenic lines without the genetic determinant can be found in FIG. 2.

The darker green seedling stem can optionally already be observed in a seedling that is one week old, wherein the hypocotyl, below the cotyledons, shows the darker stem. Preferably the stem color or chlorophyll content is compared in seedlings that are 2-3 weeks old, wherein also the stem above the cotyledons shows the darker color and/or the increase in chlorophyll content.

Throughout the growing period of the cucumber plant the stem remains darker, and also the stems of the leaves and later on of the fruits are visibly darker than from cucumber plants that do not have the genetic determinant of the invention.

In one embodiment the invention relates to a cucumber plant carrying the genetic determinant of the invention that leads to a darker green stem and/or an increase in the chlorophyll content in the seedling stage, wherein the green color of the fruits produced by said plant is at least 2 grades darker, preferably at least 3 grades darker, on a scale of 1-9, than the color of the fruit of an isogenic cucumber plant not carrying said genetic determinant, that is grown and stored under the same conditions. The color of the fruits is determined at harvest stage.

Figure 3:
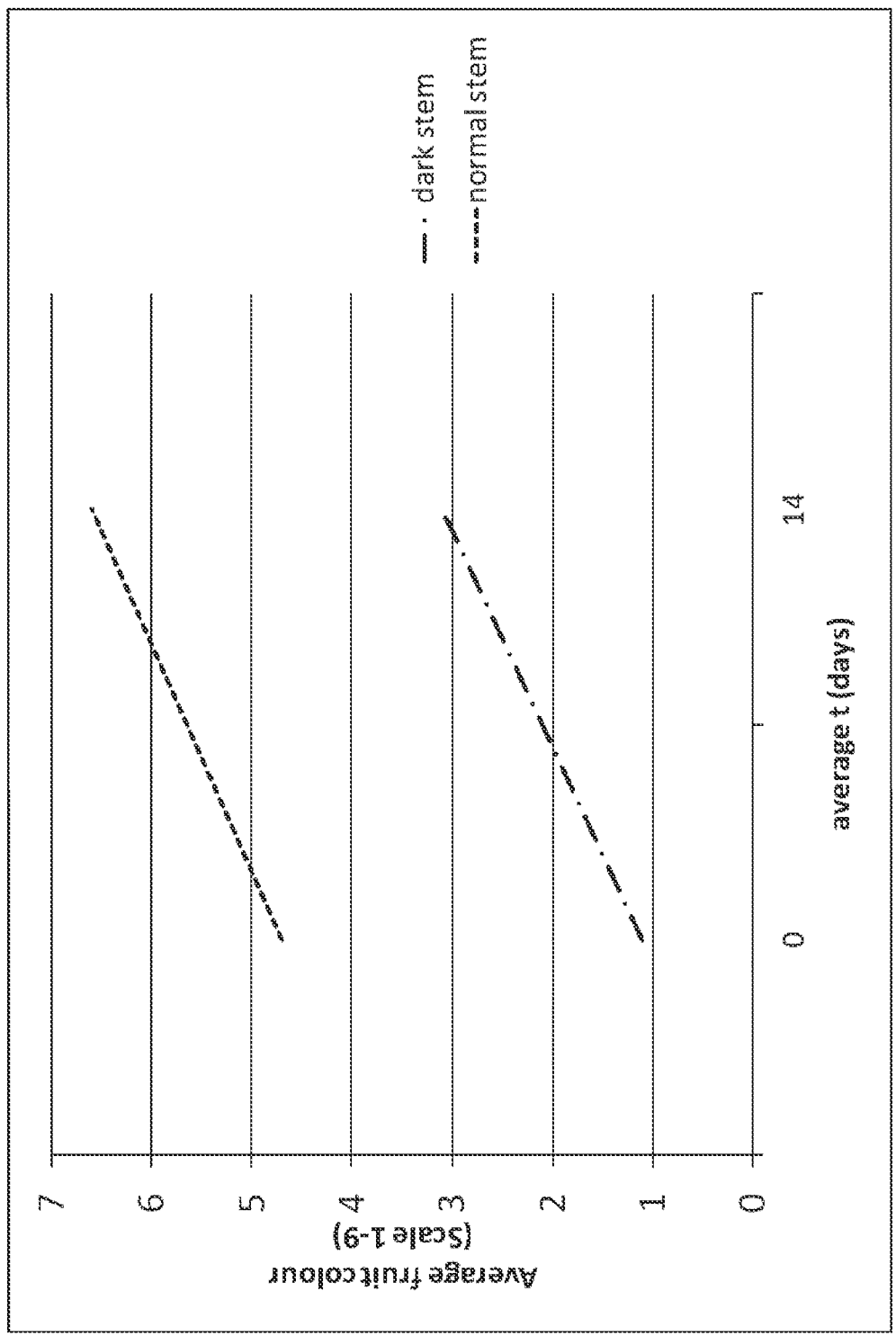
FIG. 3: average cucumber fruit color at harvest and after storage

In a preferred embodiment the color of the fruits remains at least 2 grades darker, preferably at least 3 grades darker, on a scale of 1-9, from harvest stage until at least 14 days of storage, preferably until at least 17 days of storage, more preferably until at least 19 days of storage, most preferably until at least 21 days of storage when compared to the fruit of an isogenic cucumber plant not carrying the genetic determinant, that is grown and stored under the same conditions (Table 3, FIG. 3).

After harvesting the cucumber fruits at their usual harvesting stage, cucumbers are preferably stored in climate chambers. A color scale of 1-9 can be used to visually determine the difference in color of the fruits. As used herein, a score of 1 is the darkest green fruit color, a score of 9 is a very light or yellow fruit color.

The color categories are changing gradually and can be indicated as follows: 1. extremely dark green; 2. very dark green; 3. dark green; 4. green; 5. medium green; 6. light green; 7. light green with first indication of yellowing; 8. partly yellowing; 9. yellow. A standard European greenhouse cucumber type in this scale typically has a color around score 4 or 5. Other cucumber types may have a starting color that scores somewhat higher (lighter) or lower (darker). A cucumber fruit of the invention preferably has a score of around 3, more preferably a score of around 2, most preferably a score between 1 and 2.

Optionally another scale can be used, for example a scale of 1-5, wherein the color difference is at least 1 grade, preferably at least 1.5 grades. The scores 1-5 then translate to scores 1, 3, 5, 7, and 9 of the scale of 1-9 described above.

The genetic determinant that leads to a darker green stem and/or an increase in the chlorophyll content in the seedling stage preferably also leads to an increase in the chlorophyll content of the skin of the fruit. The darker green stem can be used as a marker for the trait of the darker fruits and allows early identification of plants carrying the genetic determinant leading to such darker green fruits.

In one embodiment a cucumber plant of the invention has a darker green color of the fruit that relates to an increase in the chlorophyll content of the skin of the fruit of at least, in order of increased preference, 100 µg/g, 130 µg/g, 160 µg/g, 200 µg/g, 240 µg/g as compared to the fruit of an isogenic cucumber plant not carrying the said genetic determinant, that is grown and optionally stored under the same conditions. The comparison of chlorophyll content of the skin of the fruit is suitably done at harvest stage.

Figure 4:
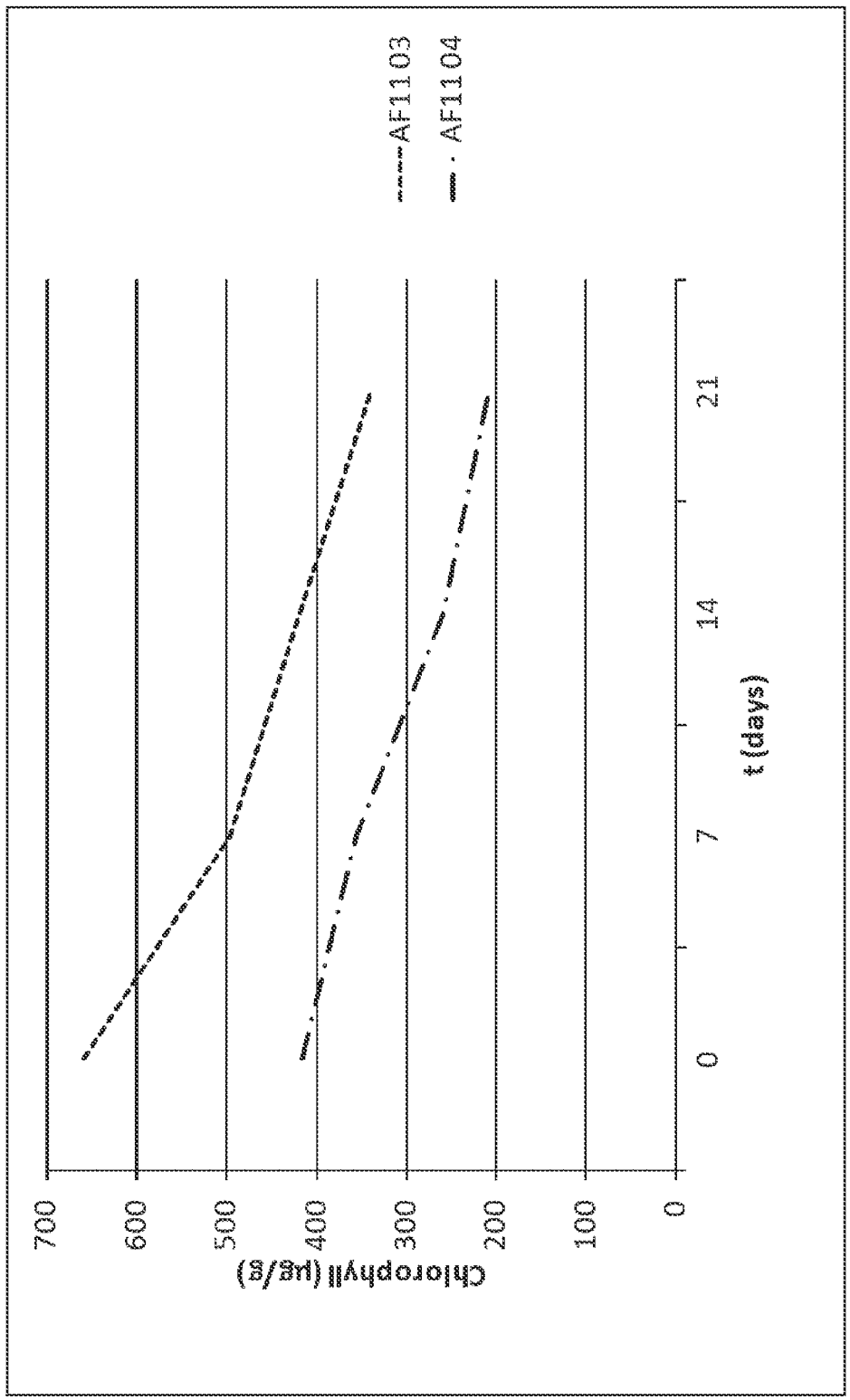
FIG. 4: chlorophyll content in skins of the cucumber fruit at harvest and after storage

In one embodiment the invention relates to a cucumber plant carrying the genetic determinant of the invention, wherein the darker green color of the fruit of the plant of the invention relates to an increase in the chlorophyll content of the skin of the fruit of at least, in order of increased preference, 30%, 40%, 50%, 60%, 70% as compared to the fruit of an isogenic cucumber plant not carrying the said genetic determinant, that is grown and optionally stored under the same conditions (Table 4, FIG. 4). The comparison of chlorophyll content of the skin of the fruit is suitably done at harvest stage. The total chlorophyll content in the skin of a cucumber fruit of the invention is suitably not higher than 1000 µg/g.

During storage of cucumber fruits, the chlorophyll content in the skin of the fruits decreases over time. The chlorophyll content in the skin of a fruit of the invention remains significantly higher during at least 14 days of storage, preferably until at least 21 days of storage, as compared to an isogenic cucumber fruit that does not carry the genetic determinant of the invention. Storage as mentioned herein is suitably done at 17° C.

The invention furthermore relates to a cell of a cucumber plant as claimed. Such cell may be either in isolated form or may be part of the complete cucumber plant or parts thereof and then still constitutes a cell of the invention because such a cell harbours in its genetic constitution the genetic information that leads to the characteristics that define the cucumber plant of the invention. Each cell of cucumber plants of the invention carries the genetic information, i.e. the genetic determinant, that leads to phenotypic expression of said trait. Such a cell of the invention may also be a regenerable cell that can be used to regenerate a new cucumber plant of the invention. In the context of this application "of the invention" means carrying a genetic determinant leading to the expression of a darker green stem in the seedling stage and a darker green fruit color. The darker green color contributes to a better storability.

The invention also relates to tissue of a plant as claimed. The tissue can be undifferentiated tissue or already differentiated tissue. Undifferentiated tissues are for example stem tips, anthers, petals, pollen and can be used in micropropagation to obtain new plantlets that are grown into new plants of the invention. The tissue can also be grown from a cell of the invention.

The invention according to a further aspect thereof relates to seeds of a plant as claimed. Although the seeds do not show the genetic trait of the cucumber plant of the invention, they harbour the genetic information, i.e. the genetic determinant, that when a plant is grown from the seeds makes this plant a plant of the invention.

The invention also relates to progeny of the plants, cells, tissues and seeds of the invention. Such progeny can in itself be plants, cells, tissues or seeds.

As used herein the word "progeny" is intended to mean the first and all further descendants from a cross with a plant of the invention that may comprise the genetic determinant that leads to a darker green stem in the seedling stage that is predictive of a darker green color of the fruits as compared to an isogenic cucumber plant not carrying the said genetic determinant. Progeny of the invention are descendants of any cross with a plant of the invention that carries the genetic determinant that leads to a darker green stem in the seedling stage that is predictive of a darker green color of the fruits.

"Progeny" also encompasses plants that carry the genetic determinant that leads to a darker green stem in the seedling stage that is predictive of a darker green color of the fruits as compared to an isogenic cucumber plant not carrying the said genetic determinant and are obtained from other plants or progeny of plants of the invention by vegetative propagation or multiplication.

The invention thus further relates to seed of the claimed plant and to parts of the plant that are suitable for sexual reproduction. Such parts are for example selected from the group consisting of microspores, pollen, ovaries, ovules, embryo sacs and egg cells. In addition, the invention relates to parts of the plant that are suitable for vegetative reproduction, in particular cuttings, roots, stems, cells, and protoplasts. The parts of the plants as mentioned above are considered propagation material.

According to a further aspect thereof the invention concerns a tissue culture of the claimed plant which is also propagation material. The tissue culture may comprise regenerable cells. Such tissue culture can be selected or derived from any part of the plant, in particular from leaves, pollen, embryos, cotyledons, hypocotyls, meristematic cells, roots, root tips, anthers, flowers, seeds and stems. The tissue culture can be regenerated into a plant carrying the genetic determinant of the invention. Suitably a regenerated plant expresses the phenotype of a darker green stem in the seedling stage that is predictive of a darker green color of the fruits as compared to an isogenic cucumber plant not carrying the said genetic determinant.

An isogenic cucumber plant of the cucumber plant of the invention can be obtained by one or more backcrosses with the parent that has received the genetic determinant of the invention. After a number of backcrosses the genetic constitution of the resulting plant is essentially the same as the genetic constitution of the starting plant except for the trait of the invention that is introgressed. The plant of the invention and the starting plant are then isogenic. Comparisons of color are made between isogenic plants to avoid any potential influence of other genes on the color.

The present invention is in particular useful for so-called long cucumber types and European greenhouse cucumber types.

The invention furthermore relates to hybrid seed and to a method of producing hybrid seed which may comprise crossing a first parent plant with a second parent plant and harvesting the resultant hybrid seed, wherein said first parent plant and/or said second parent plant has the genetic determinant of the invention. When the parent has the genetic determinant of the invention in homozygous form, the resulting hybrid plant is also a plant as claimed.

In one embodiment, the invention relates to cucumber plants of the invention that carry the genetic determinant of the invention which leads to a darker green stem in the seedling stage that is predictive of a darker green color of the fruits as compared to an isogenic cucumber plant not carrying the said genetic determinant, and that have acquired said determinant by introduction of the genetic information that is responsible for the trait from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

In one embodiment, the source from which the genetic determinant of the invention is acquired is formed by plants grown from seeds of which a representative sample was deposited under accession number NCIMB 41859, or from the deposited seeds NCIMB 41859, or from sexual or vegetative descendants thereof, or from another source which may comprise the genetic determinant that leads to the trait of the invention, or from a combination of these sources.

In a preferred embodiment, the invention relates to non-transgenic *Cucumis sativus* plants. The source for acquiring the genetic determinant of the invention, to obtain a plant of the invention that has a darker green stem which is predictive of a darker green color of the fruits, is suitably a *Cucumis sativus* plant that carries the genetic determinant of NCIMB 41859, or alternatively a plant of a *Cucumis* species that carries said gene and that can be crossed with *Cucumis sativus*. Optionally, after crossing with a related species, techniques such as embryo rescue, backcrossing, or other techniques known to the skilled person can be performed to obtain seeds of the interspecific cross, which seeds can be used as the source for further development of a non-transgenic *Cucumis sativus* plant that shows a darker green stem in the seedling stage that is predictive of a darker green color of the fruits as compared to an isogenic cucumber plant not carrying the said genetic determinant.

The invention also relates to the germplasm of plants of the invention. The germplasm is constituted by all inherited characteristics of an organism and according to the invention encompasses at least the trait of the invention. The germplasm can be used in a breeding program for the development of cucumber plants having a darker green stem that is predictive of a darker green color of the fruits as compared to an isogenic cucumber plant not carrying the said genetic determinant. The use of the germplasm that may comprise the genetic determinant leading to a darker green stem and darker green fruits in breeding is also part of the present invention.

The invention also concerns the use of the genetic determinant leading to the trait of the invention, which genetic determinant is genetically linked with any of the molecular markers E13/M51-143.48 and/or E13/M51-154.68 and/or E16/M60-086.74, for the development of cucumber plants that have a darker green stem in the seedling stage that is predictive of a darker green color of the fruits at harvest stage as compared to an isogenic cucumber plant not carrying the said genetic determinant The invention also relates to a cucumber fruit that is produced by a plant of the invention. The invention further relates to a food product, which may comprise the fruit of a cucumber plant as claimed, or parts thereof. The invention also relates to a food product in processed form.

In one aspect the invention relates to a method for production of a cucumber plant which may comprise the genetic determinant that leads to a darker green stem in the seedling stage that is predictive of a darker green color of the fruits as compared to an isogenic cucumber plant not carrying the said genetic determinant, which may comprise:

a) crossing a plant which may comprise the genetic determinant of the invention, representative seed of which plant was deposited as NCIMB 41859, with a plant not comprising the genetic determinant to obtain an F1 population;

b) optionally performing one or more rounds of selfing and/or crossing a plant from the F1 to obtain a further generation population;

c) selecting a plant that may comprise the genetic determinant that results in a darker green stem in the seedling stage that is predictive of a darker green color of the fruits as compared to an isogenic cucumber plant not carrying the said genetic determinant, suitably by using molecular markers linked to the genetic determinant. The plant can also be selected by visual inspection of the stem of the seedling for a darker green color than the parent plant that does not comprise the genetic determinant of the invention.

The invention additionally provides a method of introducing another desired trait into a cucumber plant which may comprise the trait of the invention, which may comprise:

a) crossing a cucumber plant which may comprise the genetic determinant that leads to a darker green stem in the seedling stage that is predictive of a darker green color of the fruits as compared to an isogenic cucumber plant not carrying the said genetic determinant, representative seed of which was deposited with the NCIMB under deposit number NCIMB 41859, with a second cucumber plant that may comprise the other desired trait to produce F1 progeny;

b) selecting an F1 progeny that may comprise genetic determinants for the trait of the invention and for the desired trait;

c) crossing the selected F1 progeny with either parent, to produce backcross progeny;

d) selecting backcross progeny which may comprise genetic determinants for the desired trait and for the trait of the invention; and e) optionally repeating steps c) and d) one or more times in succession to produce selected fourth or higher backcross progeny that may comprise the desired trait and the trait of the invention. The invention includes a cucumber plant produced by this method and the cucumber fruit obtained therefrom.

Optionally selfing steps are performed after any of the crossing or backcrossing steps. Selection for a plant which may comprise the genetic determinant of the invention and the desired trait can alternatively be done following any crossing or selfing step of the method.

In one embodiment the plant of the invention which may comprise the genetic determinant either homozygously or heterozygously is a plant of an inbred line, a hybrid, a doubled haploid, or of a segregating population.

The invention further provides a method for the production of a cucumber plant which may comprise a darker green stem as defined herein by using a doubled haploid generation technique to generate a doubled haploid line that homozygously may comprise the genetic determinant that leads to the darker green stem, which doubled haploid line can be crossed with a line that lacks the said genetic determinant to generate a plant of the invention that may comprise the genetic determinant heterozygously.

The invention also relates to a method for the production of a cucumber plant which may comprise the genetic determinant that leads to the darker green stem of the invention, by using a seed that may comprise the genetic determinant in its genome that leads to the darker green stem of the invention for growing the said cucumber plant. The seeds are suitably seeds of which a representative sample was deposited with the NCIMB under deposit number NCIMB 41859.

The invention also relates to a method for seed production which may comprise growing cucumber plants which may comprise the genetic determinant of the invention, which results in the phenotypic trait of the invention, allowing the plants to produce seeds, and harvesting those seeds. Production of the seeds is suitably done by crossing or selfing.

In one embodiment, the invention relates to a method for the production of a cucumber plant which may comprise a darker green stem that is predictive of a darker green fruit color by using tissue culture. The invention furthermore relates to a method for the production of a cucumber plant which may comprise the darker green stem of the invention, by using vegetative reproduction.

In one embodiment, the invention relates to a method for the production of a cucumber plant which may comprise the darker green stem by using a method for genetic modification to introduce the genetic determinant of the invention that leads to a darker green stem in the seedling stage that is predictive of a darker green color of the fruits as compared to an isogenic cucumber plant not carrying the said genetic determinant into the cucumber plant.

The invention provides preferably a cucumber plant showing a darker green stem in the seedling stage that is predictive of a darker green color of the fruits as compared to an isogenic cucumber plant not carrying the said genetic determinant, which plant is obtainable by any of the methods herein described.

The invention also relates to a method for the production of cucumber fruits, which may comprise growing cucumber plants with a darker green stem as described herein and allowing them to produce cucumber fruits and optionally harvesting the fruits.

The term 'genetic determinant' and 'genetic determinants' as used herein encompasses one or more QTLs, genes, or alleles. These terms are used interchangeably.

A genetic determinant can be identified by the use of a molecular marker. A genetic determinant can alternatively be identified by the position on a genetic map, or by indication of the location on a linkage group or chromosome. When a genetic determinant is not linked to a specific molecular marker any longer, but its position on a chromosome as defined on a genetic map is unaltered, this genetic determinant is still the same as when it was linked to the molecular marker. The genetic trait that it confers is therefore also still the same.

The 'genetic trait' is the trait or characteristic that is conferred by the genetic determinant. The genetic trait can be identified phenotypically, for example by performing a bio-assay. However, also plant stages for which no phenotypic assay can be performed do carry the genetic information that leads to the genetic trait. 'Trait' or 'phenotypic trait' can be used instead of 'genetic trait'.

In the absence of molecular markers, or in the instance that recombination between the genetic determinant and the marker has taken place so that the marker is not predictive anymore, equivalence of genetic determinants can be determined by an allelism test. To perform an allelism test, a tester plant which is homozygous for the known determinant of the invention is crossed with material to be tested that is also homozygous for its genetic determinant. When no segregation for the trait to be observed is present in the F2 of the cross, the genetic determinants have been proven to be equivalent or the same.

When more than one gene is responsible for a certain trait, and an allelism test is done to determine equivalence, the skilled person doing the test has to make sure that all relevant genes are present homozygously for the test to work properly.

The invention will be further illustrated in the Examples that follow.

Marker Information

The primers used for the AFLP markers are standardized and the sequences to combine can be found at for example the following website: ttp://wheat.pw.usda.gov/ggpages/keygeneAFLPs.html.

EXAMPLES

Example 1

Phenotypic Characterization of the Invention

To obtain cucumber fruits with an increased storability, one aspect forms the improvement of fruit color, wherein a darker green fruit color is favored. This is however a complex goal to attain in breeding.

In the germplasm of the cucumber breeding program, a plant was developed that already several days after germination showed an unusually dark seedling stem. This phenotypic trait was monitored during the subsequent development of the plant. It appeared that succeeding plant stems, including the main stem, but also the stems, or petioles, of the leaves and later on of the fruits, displayed an unusually dark color.

It was decided to explore whether there existed a potential benefit of the darker green stems, which was expected to be connected to an increase in the chlorophyll content, in relation to the color of the fruits. Surprisingly it was found that the plants that showed a darker green stem color also had a darker green fruit color. No relation between fruit and stem color in cucumber has ever been established earlier.

The plant which may comprise the darker green stem color was crossed with a plant with a normal stem color to observe the inheritance. It was clear that the F1 also showed a darker green stem color, which confirms a dominant inheritance of the phenotype of this trait (FIG. 1). The fruits of said plants were compared as well, and the inheritance of the darker green fruit color was also determined to be dominant.

After selfing the F1 plants, segregation data from F2 and further generations corresponded to the presence of a monogenetic determinant for this trait.

Example 2

Biochemical Characterization of the Invention

The stems of the seedlings that were developed in Example 1 were analysed for chlorophyll content. To obtain reliable comparisons, different plants containing the trait homozygously were measured, and comparison was done with isogenic lines which are genetically the same but lack the genetic determinant of the invention.

The analysis confirmed that the darker green seedling stems were a result of an increase in chlorophyll content. Both chlorophyll components that were present, chlorophyll a and chlorophyll b, were increased, resulting in a significant increase in total chlorophyll content (FIG. 2).

The chlorophyll content of the seedling stem of the F1 was measured as well. This showed that in the seedling stem the biochemical feature also inherited as a completely dominant trait. The increase in chlorophyll content compared to a normal stem color was clearly present, and was even slightly higher than the content of the parent in which the genetic determinant was homozygously present.

Again, also the observation was done on fruits of plants with an increased chlorophyll content in the stem. The measurements of the darker green fruits of these plants validated that the darker color was once more the result of an increase in chlorophyll content in the skin of the fruits, and that this feature inherited dominantly. A clear correlation was therefore established between an increase in chlorophyll contents of stems and fruits of plants of the invention.

Example 3

Molecular Characterization of the Invention

A population of 90 DH plants was developed from an F1 between dark stem and normal stem. 48 DH individuals were eventually used to identify AFLP markers linked to the trait, using a Bulk Segregant Analysis (BSA) approach. Half of the individuals had the dark green stem phenotype, and the other half were normal green. Both parents of the population were included in the analysis.

Two bulks of 10 individuals were initially used for screening with 192 primer combinations (PC's). From this screen, six PC's were identified to be verified on the 48 DH individuals, which resulted in 7 co-dominantly scored AFLP markers. The generated AFLP markers were further analysed for linkage to the trait of the invention. Finally, 3 AFLP markers were determined to be completely associated with the dark stem trait in this population, which markers were E13/M51-143.48, E13/M51-154.68, and E16/M60-086.74

The identified molecular markers can be used to identify the presence of the genetic determinant of the invention in plants grown from seeds as deposited under NCIMB number 41859. Other plants that may comprise the same genetic determinant of the invention might also be linked to the said markers, but can optionally also be linked to any other molecular marker that is polymorphic in a certain population.

The cucumber plant of the invention was further analyzed for the presence of known shelf life QTLs, as defined in WO2007/042070. Presence of QTL1 of said application was assayed by determining whether SEQ ID No. 9, as indicated in WO2007/042070 to be QTL1, was present in a cucumber plant of the present invention, such as the deposit. In addition, the presence of QTL2 was assayed by determining the presence of the marker defined in WO2007/042070 as a marker of about 137 base pairs consisting from 5' to 3' of a first primer having SEQ ID No:5, a cucumber genomic fragment, and a second primer having SEQ ID No: 6. For the second marker through which said QTL2 could be identified, no polymorphisms were found in a very large set of cucumber plants.

Since WO2007/042070 does not provide a deposit for reference, a prior art cucumber variety that comprised SEQ ID No. 9 as well as QTL2 of said application, was identified by marker analysis performed at KeyGene (Wageningen, Netherlands). The stem color of this particular plant was compared with a cucumber plant of the present invention, in particular with the deposit. Results are presented in Table 2.

TABLE 2

| Cucumis sativus | QTL 1 - SEQ ID No. 9 | QTL2 marker | Stem color |
|---|---|---|---|
| Beluga F1 | H | A | Green-medium: 4-5 |
| Azabache F1 | A | A | Green-medium: 4-5 |
| NCIMB 41859 | B | B | Very dark: 2 |

A means the marker or sequence is present homozygously

H means the marker or sequence is present heterozygously

B means the marker or sequence is absent

Example 4

Fruit Color and Chlorophyll During Storage

Fruits of plants of the invention were observed for their performance during storage. The fruits were compared with fruits from isogenic plants that were genetically the same but did not comprise the genetic determinant of the invention.

Initial fruit color was scored for fruits from both types, using a score of 1-9, in which a score of 1 was the darkest green to be observed, and 9 was a yellowed cucumber fruit. The fruits were subsequently stored at 17° C. for 10 up to 19 days and graded again at the end. Fruits of the invention were at least 3 grades darker at the harvesting date, on average even 3.6 grades darker, and remained at least 2.5 grades darker after storage, on average even 3.5 grades darker (Table 3).

TABLE 3

Fruit color during storage

| days | start | end | color decrease dark stem | start | end | color decrease normal stem |
|---|---|---|---|---|---|---|
|  |  | fruit color dark stem |  |  | fruit color normal stem |  |
| 17 | 1.3 | 2.5 | 1.2 | 4.2 | 6.4 | 2.2 |
| 15 | 1.1 | 2.3 | 1.2 | 4.7 | 6.1 | 1.4 |
| 10 | 1.2 | 2 | 0.8 | 4.9 | 5.6 | 0.7 |
| 19 | 1 | 5.2 | 4.2 | 4.5 | 7.9 | 3.4 |
| 14 | 1 | 3.5 | 2.5 | 4.8 | 7 | 2.2 |
| 12 | 1 | 2.8 | 1.8 | 4.8 | 6.8 | 2 |
| Average 14 | 1.1 | 3.1 | 2 | 4.7 | 6.6 | 2 |

1 = darkest green

9 = lightest/yellow

As can be seen from the data, cucumber fruits of the invention at the end of storage still possessed a color that was darker, which is perceived to be better, than just harvested cucumber fruits that did not comprise the genetic determinant of the invention. Therefore the darker green stem of plants of the invention is surprisingly but clearly correlated with an improvement in initial fruit color, and in fruit color during storage, of cucumber fruits.

In addition, chlorophyll content in the skins of the fruits was measured after harvest, after 7 days, 14 days, and 21 days. The measurements clearly confirmed that the chlorophyll content of dark green fruits of the invention started out significantly higher when compared to an isogenic line lacking the genetic determinant of the invention, and remained significantly higher during storage up to 21 days (Table 4, FIG. 4).

TABLE 4

Chlorophyll content in fruit skin

| line dark stem | t (days) | chlorophyll (µg/g) in fruit skin | line normal stem | chlorophyll (µg/g) in fruit skin |
|---|---|---|---|---|
| AF11 03 | 0 | 658 | AF11 04 | 415 |
| AF11 03 | 7 | 496 | AF11 04 | 355 |
| AF11 03 | 14 | 418 | AF11 04 | 259 |
| AF11 03 | 21 | 340 | AF11 04 | 209 |

The chlorophyll measurements of the skins of the fruits confirmed the correlation between dark green stems and/or stems higher in chlorophyll content on the one hand, and dark green fruit color and/or higher chlorophyll content in the skins of the fruits at harvest and during storage up till 21 days on the other hand.

Example 5

Transfer of the Trait of the Invention

In an F2 population as was for instance developed in Example 1, plants comprising darker green stem could be selected phenotypically, but to immediately obtain plants that contained the trait homozygously, markers as described in Example 3 were used. The trait of the invention appeared to be easily transferable into other backgrounds, as can also be seen in FIG. 2. The presence of the genetic determinant was confirmed to result in a darker green seedling stem and darker green fruits as compared to the parent that was used in the cross and did not yet contain the genetic determinant of the invention.

The genetic determinant and phenotypic trait of the invention have therefore shown to be usable in various backgrounds to improve the initial fruit color of cucumbers, and at the same time improve the quality of cucumber fruits during a storage time of at least 10, up to at least 21 days.

The invention is further described by the following numbered paragraphs:

1. Cucumber plant of the species *Cucumis sativus* carrying a genetic determinant that leads to a darker green stem in the seedling stage that is predictive of a darker green color of the fruits as compared to an isogenic cucumber plant not carrying the said genetic determinant, which genetic determinant is as comprised in a cucumber plant representative seed of which was deposited with the NCIMB under deposit number NCIMB 41859.

2. Cucumber plant of paragraph 1, wherein the genetic determinant is introgressed from a cucumber plant of which representative seed has been deposited with the NCIMB under deposit number NCIMB 41859.

3. Cucumber plant of paragraph 1 or 2, obtainable by crossing a first cucumber plant with a second cucumber plant, wherein at least one of the said plants is grown from seed of which a representative sample was deposited under deposit number NCIMB 41859, or a progeny plant thereof, optionally selfing the resulting F1, and selecting for plants that have one or more of the following characteristics:
   a) they have at the seedling stage a darker green stem as compared to the stem of a seedling of an isogenic cucumber plant not carrying the said genetic determinant, which darker green stem is predictive of the production of fruits having a darker green color at harvest stage as compared to the fruits of an isogenic cucumber plant not carrying the said genetic determinant under the same conditions, and/or
   b) they have at the seedling stage an increase in the content of chlorophyll in the stem as compared to the stem of a seedling of an isogenic cucumber plant not carrying the said genetic determinant, which increase in the content of chlorophyll is predictive of the production of fruits having a darker green color at harvest stage as compared to the fruits of an isogenic cucumber plant not carrying the said genetic determinant under the same conditions.

4. Cucumber plant of any one of the paragraphs 1-3, wherein the chlorophyll content in the stem of the plant at seedling stage is at least, in order of increased preference, 40 µg/g, 70 µg/g, 100 µg/g, 120 µg/g, 150 µg/g, 180 µg/g, 200 µg/g higher than the chlorophyll content in the stem of an isogenic cucumber plant at seedling stage not carrying the said genetic determinant, that is grown under the same conditions.

5. Cucumber plant of any one of the paragraphs 1-3, wherein the chlorophyll content in the stem of the plant at seedling stage is at least, in order of increased preference, 30% higher, 60% higher, 90% higher, 120% higher, 150% higher, 180% higher, 200% higher, 230% higher, 270% higher, 300% higher than the chlorophyll content in the stem of an isogenic cucumber plant at seedling stage not carrying the said genetic determinant, that is grown under the same conditions.

6. Cucumber plant of any of the paragraphs 1-5, wherein the green color of the fruit from harvest stage until at least 14 days after storage, preferably until 21 days after storage, is at least 2 grades darker, preferably at least 3 grades darker, on a scale of 1-9, than the color of the fruit of an isogenic cucumber plant not carrying the said genetic determinant, that is grown and stored under the same conditions.

7. Cucumber plant of any of the paragraphs 1-6, wherein the darker green color of the fruit relates to an increase in the chlorophyll content of the skin of the fruit of at least, in order of increased preference, 100 µg/g, 130 µg/g, 160 µg/g, 200 µg/g, 240 µg/g as compared to the fruit of an isogenic cucumber plant not carrying the said genetic determinant, that is grown under the same conditions.

8. Cucumber plant of any of the paragraphs 1-7, wherein the darker green color of the fruit at harvest stage relates to an increase in the chlorophyll content of the skin of the fruit of at least, in order of increased preference, 30%, 40%, 50%, 60%, 70% as compared to the fruit of an isogenic cucumber plant not carrying the said genetic determinant, that is grown under the same conditions.

9. Cucumber plant of any of the paragraphs 1-8, wherein the said genetic determinant is genetically linked with any of the molecular markers E13/M51-143.48 and/or E13/M51-154.68 and/or E16/M60-086.74 in seed of deposit number NCIMB 41859 and optionally in the plant as paragraphed.

10. Cucumber seed, wherein the plant that can be grown from the seed comprises the genetic determinant as defined in any of the paragraphs 1-9.

11. Progeny of a cucumber plant of any one of the paragraphs 1-9 or of cucumber seed of paragraph 10, comprising the genetic determinant as defined in any of the paragraphs 1-9.

12. Propagation material suitable for producing a plant of any one of the paragraphs 1-9, wherein the propagation material is suitable for sexual reproduction, and is in particular selected from microspores, pollen, ovaries, ovules, embryo sacs and egg cells, or is suitable for vegetative reproduction, and is in particular selected from cuttings, roots, stems, cells, protoplasts, or is suitable for tissue cultures of regenerable cells, and is in particular selected from leaves, pollen, embryos, cotyledons, hypocotyls, meristematic cells, roots, root tips, anthers, flowers, seeds and stems, wherein the plant produced from the propagation material comprises the genetic determinant as defined in any of the paragraphs 1-9.

13. Food product, comprising the cucumber fruit of a plant of any one of the paragraphs 1-9, or parts thereof, optionally in processed form.

14. Use of a plant of any one of the paragraphs 1-9 or 11, or of a plant produced from the seed of paragraph 10 or from the propagation material of paragraph 12, as germplasm in a breeding program for the development of cucumber plants that have a darker green stem in the seedling stage that is predictive of a darker green color of the fruits at harvest stage as compared to an isogenic cucumber plant not carrying the said genetic determinant.

15. Use of molecular markers E13/M51-143.48 and/or E13/M51-154.68 and/or E16/M60-086.74 for use in the development of cucumber plants that have a darker green stem in the seedling stage that is predictive of a darker green color of the fruits at harvest stage as compared to an isogenic cucumber plant not carrying the said genetic determinant.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A cucumber plant of the species *Cucumis sativus* carrying a QTL that leads to a chlorophyll content of between 140-1000 μg/g in the stem in the seedling stage that is predictive of a dark green color of the fruit, which QTL is present in a cucumber plant representative seed of which was deposited with the NCIMB under deposit number NCIMB 41859, and wherein the OTL is genetically linked with molecular marker E13/M51-143.48, which is absent from the QTL on chromosome 3 from position 39231231 bp to position 39231357 bp in the cucumber reference genome, and molecular marker E13/M51-154.68, which is comprised in the QTL on chromosome 3 from position 39231231 bp to position 39231357 bp in the cucumber reference genome, and molecular marker E16/M60-086.74, which is comprised in the QTL on chromosome 3 from position 39750868 to position 39750927 in the cucumber reference genome, whereby the length of the QTL is from molecular marker E13/M51-154.68, starting on position 39231231, to molecular marker E16/M60-086.74, ending on position 39750927.

2. The cucumber plant as claimed in claim 1, wherein the QTL is introgressed from a cucumber plant of which representative seed has been deposited with the NCIMB under deposit number NCIMB 41859 or a progeny plant thereof comprising the QTL as present in deposit number NCIMB 41859 as defined in claim 1.

3. A cucumber plant as claimed in claim 1, obtained by crossing a first cucumber plant with a second cucumber plant, wherein at least one of the said plants is grown from seed of which a representative sample was deposited under deposit number NCIMB 41859, or a progeny plant thereof comprising the QTL as present in deposit number NCIMB 41859 as defined in claim 1, optionally selfing the resulting F1, and selecting for plants that have the QTL that leads to a chlorophyll content of between 140-1000 μg/g in the stem in the seedling stage that is predictive of a dark green color of the fruit.

4. A cucumber seed, wherein the plant that can be grown from the seed comprises the QTL as defined in claim 1.

5. A progeny of a cucumber plant as claimed in claim 1, comprising a QTL that leads to a chlorophyll content of between 140-1000 μg/g in the stem in the seedling stage that is predictive of a dark green color of the fruit, which QTL is as defined in claim 1.

6. A progeny of a cucumber plant grown from the seed of claim 4, comprising a QTL that leads to a chlorophyll content of between 140-1000 μg/g in the stem in the seedling stage that is predictive of a dark green color of the fruit, which QTL is as defined in claim 1.

7. A propagation material suitable for producing a plant as claimed in claim 1, wherein the propagation material is suitable for sexual reproduction and wherein the plant produced from the propagation material comprises the QTL as defined in claim 1.

8. The propagation material of claim 7, wherein the propagation material comprises a microspore, pollen, ovary, ovule, embryo sac or egg cell.

9. A propagation material suitable for producing a plant as claimed in claim 1, wherein the propagation material is suitable for vegetative reproduction and wherein the plant produced from the propagation material comprises the QTL as defined in claim 1.

10. The propagation material of claim 9, wherein the propagation material comprises a cutting, root, stem, cell or protoplast.

11. A propagation material suitable for producing a plant as claimed in claim 1, wherein the propagation material is suitable for tissue cultures of regenerable cells and wherein the plant produced from the propagation material comprises the QTL as defined in claim 1.

12. The propagation material of claim 11, wherein the propagation material comprises a leaf, pollen, embryo, cotyledon, hypocotyl, meristematic cell, root, root tip, anther, flower, seed or stem.

13. A food product comprising the cucumber fruit of a plant as claimed in claim 1, or parts thereof, optionally in processed form.

14. A method for production of a cucumber plant having a trait of a chlorophyll content of between 140-1000 μg/g in the stem in the seedling stage that is predictive of a dark green color of the fruit, comprising:
  a) crossing a plant grown from seed deposited as NCIMB 41859 or from a progeny thereof comprising the QTL as present in deposit number NCIMB 41859 as defined in claim 1 that leads to a chlorophyll content of between 140-1000 μg/g in the stem in the seedling stage that is predictive of a dark green color of the fruit, with a plant not having the QTL to obtain a F1 population;
  b) optionally performing one or more rounds of selfing and/or crossing a plant from the F1 to obtain a further generation population; and
  c) selecting a plant that comprises the QTL as defined in claim 1 that leads to a chlorophyll content of between 140-1000 μg/g in the stem in the seedling stage that is predictive of a dark green color of the fruit.

\* \* \* \* \*